US009823260B2

(12) United States Patent
Puthenveedu et al.

(10) Patent No.: US 9,823,260 B2
(45) Date of Patent: Nov. 21, 2017

(54) METHOD TO INCREASE BIOAVAILABILITY OF THE DELTA-OPIOID RECEPTOR FOR MANAGEMENT OF PAIN AND NEUROPSYCHIATRIC DISORDERS

(71) Applicant: CARNEGIE MELLON UNIVERSITY, a Pennsylvania Non-Profit Corporation, Pittsburgh, PA (US)

(72) Inventors: Manojkumar A. Puthenveedu, Pittsburgh, PA (US); Daniel J. Shiwarski, Pittsburgh, PA (US); Amynah Pradhan, Chicago, IL (US)

(73) Assignees: Carnegie Mellon University, a Pennsylvania Non-Profit Corporation, Pittsburgh, PA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/799,276

(22) Filed: Jul. 14, 2015

(65) Prior Publication Data
US 2016/0008430 A1 Jan. 14, 2016

Related U.S. Application Data

(60) Provisional application No. 61/999,021, filed on Jul. 14, 2014.

(51) Int. Cl.
A61K 38/16 (2006.01)
G01N 33/94 (2006.01)
A61K 45/06 (2006.01)
A61K 31/167 (2006.01)

(52) U.S. Cl.
CPC ....... G01N 33/9486 (2013.01); A61K 31/167 (2013.01); A61K 45/06 (2013.01); G01N 2333/726 (2013.01)

(58) Field of Classification Search
None
See application file for complete search history.

(56) References Cited

PUBLICATIONS

Bodnar, R. J., "Endogenous opiates and behavior: 2007." Peptides 29,2292-2375 (2008).
He, L. et al., "Regulation of opioid receptor trafficking and morphine tolerance by receptor oligomerization." Cell 108, 271-282 (2002).
Martini, L. et al., "The role of mu opioid receptor desensitization and endocytosis in morphine tolerance and dependence." Current Opinion in Neurobiology 17, 556-564 (2007).
Kim, J. A. et al., "Morphine-Induced Receptor Endocytosis in a Novel Knockin Mouse Reduces Tolerance and Dependence." Current Biology 18, 129-135 (2008).
Ignatova, E. G. E. et al., "Requirement of receptor internalization for opioid stimulation of mitogen-activated protein kinase: biochemical and immunofluorescence confocal microscopic evidence." J. Neurosci. 19, 56-63 (1999).
Whistler, J. L., "A Phosphorylation-regulated Brake Mechanism Controls the Initial Endocytosis of Opioid Receptors but is not Required for Post-endocytic Sorting to Lysosomes." Journal of Biological Chemistry 276, 34331-34338 (2001).
Whistler, J. L., "Modulation of Postendocytic Sorting of G Protein-Coupled Receptors." Science 297, 615-620 (2002).
Tanowitz, M., "A Novel Endocytic Recycling Signal That Distinguishes the Membrane Trafficking of Naturally Occurring Opioid Receptors." Journal of Biological Chemistry 278, 45978-45986 (2003).
Berry, A. et al., "Brain and Behavioral Plasticity." Neural Plasticity 2012, 1-9 (2012).
Taiwo, Y. O. et al., "Hyperalgesia induced in the rat by the amino-terminal octapeptide of nerve growth factor." Proc. Natl. Acad. Sci. U.S.A. 88, 5144-5148 (1991).
Boue-Grabot, E. et al., "A protein kinase C site highly conserved in P2X subunits controls the desensitization kinetics of P2X(2) ATP-gated channels." J. Biol. Chem. 275, 10190-10195 (2000).
Duvernay, M. T., "A Conserved Motif for the Transport of G Protein-coupled Receptors from the Endoplasmic Reticulum to the Cell Surface." Journal of Biological Chemistry 279, 30741-30750 (2004).
Dong, C. et al., "Regulation of G protein-coupled receptor export trafficking." Biochimica et Biophysica Acta (BBA)—Biomembranes 1768, 853-870 (2007).
Puthenveedu, M. A. et al., "Sequence-Dependent Sorting of Recycling Proteins by Actin-Stabilized Endosomal Microdomains." Cell 143, 761-773 (2010).
Pradhan, A. A. A. et al., "In Vivo Delta Opioid Receptor Internalization Controls Behavioral Effects of Agonists." PLoS ONE 4, e5425 (2009).
Pizzo, P. A. et al., "Alleviating suffering 101—pain relief in the United States." N Engl J Med 366, 197-9 (2012). doi:10.1056/NEJMp1109084.
Institute of Medicine (US) Committee on Advancing Pain Research, Care, and Education Relieving Pain in America: A Blueprint for Transforming Prevention, Care, Education, and Research. Relieving Pain in America: A Blueprint for Transforming Prevention, Care, Education, and Research (National Academies Press (US): Washington (DC), 2011).
Nicholson, B. et al., "Comorbidities in chronic neuropathic pain." Pain Med 5 Suppl 1, S9-S27 (2004).
Stein, C., "Opioids, sensory systems and chronic pain." Eur J Pharmacol 716, 179-87 (2013).doi:10.1016/j.ejphar.2013.01.076.
Williams, J. T. et al., "Regulation of μ-opioid receptors: desensitization, phosphorylation, internalization, and tolerance." Pharmacol Rev 65, 223-54 (2013).doi:10.1124/pr.112.005942.

(Continued)

Primary Examiner — Christine J Saoud
Assistant Examiner — Jon M Lockard
(74) Attorney, Agent, or Firm — Michael G. Monyok; David G. Oberdick

(57) ABSTRACT

Described herein is a method to induce surface trafficking of the delta-Opioid Receptor (DOR) and its applications, including, leveraging the antinociceptive potential of DOR agonists to treaty neurologic disorders and to be analgesics without the adverse consequences normally associated with chronic treatment by MOR agonists by inducing surface trafficking of the delta-Opioid Receptor (DOR) and screening compounds to identify additional targets for stimulated DOR delivery.

8 Claims, 11 Drawing Sheets

(56) References Cited

PUBLICATIONS

Pasternak, G. W., "Opioids and their receptors: Are we there yet?" Neuropharmacology 76 Pt B, 198-203 (2014). doi:10.1016/j.neuropharm.2013.03.039.

Trends & Statistics | National Institute on Drug Abuse. NIDA at <http://www.drugabuse.gov/related-topics/trends-statistics>.

Centers for Disease Control and Prevention (CDC) "CDC grand rounds: prescription drug overdoses—a U.S. epidemic." MMWR Morb Mortal Wkly Rep 61, 10-3 (2012).

"Monitoring the Future 2013, Teen drug use." NIDA (2014).at <http://www.drugabuse.gov/related-topics/trends-statistics/infographics/monitoring-future-2013- survey-results>.

"Abuse of Prescription Pain Medications Risks Heroin Use." NIDA.

"Drug Overdose in the United States: A Fact Sheet." CDC (2013).at <http://www.cdc.gov/homeandrecreationalsafety/overdose/facts.html>.

Beletsky, L. et al., "Prevention of fatal opioid overdose." JAMA 308, 1863-4 (2012).doi:10.1001/jama.2012.14205.

Nucklos, T. K. et al. "Opioid prescribing: a systematic review and critical appraisal of guidelines for chronic pain." Ann Intern Med 160, 38-47 (2014).doi:10.7326/0003-4819-160-1-201401070-00732.

Centers for Disease Control and Prevention (CDC) "Vital signs: risk for overdose from methadone used for pain relief—United States" 1999-2010. MMWR Morb Mortal Wkly Rep 61, 493-7 (2012).

Lutz, P. E. et al., "The multiple facets of opioid receptor function: implications for addiction." Curr Opin Neurobiol 23, 473-9 (2013). doi:10.1016/j.conb.2013.02.005.

Pasternak, G. W., "Opiate Pharmacology and Relief of Pain." J Clin Oncol (2014).doi:10.1200/JCO.2013.53.1079.

Walwyn, W. M. et al., "Opioid pharmaceuticals and addiction: the issues, and research directions seeking solutions." Drug Alcohol Depend 108, 156-65 (2010).doi:10.1016/j.drugalcdep.2010.01.001.

Robison, A. J. et al., "Transcriptional and epigenetic mechanisms of addiction." Nat Rev Neurosci 12, 623-37 (2011). doi:10.1038/nm3111.

Bohn, L. M. et al., "Mu-opioid receptor desensitization by beta-arrestin-2 determines morphine tolerance but not dependence." Nature 408, 720-3. (2000).doi:10.1038/35047086.

Von Zastrow, M., "A cell biologist's perspective on physiological adaptation to opiate drugs." Neuropharmacology 47 Suppl 1, 286-92—(2004).

Gaveriaux-Ruff, C. et al., "Delta opioid receptor analgesia: recent contributions from pharmacology and molecular approaches." Behav Pharmacol 22, 405-14 (2011).doi:10.1097/FBP.0b013e32834a1f2c.

Cahill, C. M. et al., "Trafficking of delta-opioid receptors and other G-protein-coupled receptors: implications for pain and analgesia." Trends Pharmacol Sci 28, 23-31 (2007).doi:10.1016/j.tips.2006.11.003.

Mika, J. et al., "The role of delta-opioid receptor subtypes in neuropathic pain." Eur J Pharmacol 415, 31-7 (2001).

Rapaka, R. S. et al., "Development of delta opioid peptides as nonaddicting analgesics." Pharm Res 8, 1-8 (1991).

Scherrer, G. et al., "Dissociation of the opioid receptor mechanisms that control mechanical and heat pain." Cell 137, 1148-59 (2009). doi:10.1016/j.cell.2009.04.019.

Chu Sin Chung, P. et al., "Delta opioid receptors in brain function and diseases." Pharmacol Ther 140, 112-20 (2013).doi:10.1016/j.pharmthera.2013.06.003.

Bie, B. et al., "Nerve growth factor-regulated emergence of functional delta-opioid receptors." J Neurosci 30, 5617-28 (2010). doi:10.1523/JNEUROSCI.5296-09.2010.

Pradhan, A. A. et al., "Ligand-Directed Signaling Within the Opioid Receptor Family." Br J Pharmacol (2012). doi:10.1111/j.1476-5381.2012.02075.x.

Van Rijn, R. M. et al., "Pharmacological traits of delta opioid receptors: pitfalls or opportunities?" Psychopharmacology (Berl) 228, 1-18 (2013).doi:10.1007/s00213-013-3129-2.

Danielsson, I. et al., "Electroencephalographic and convulsant effects of the delta opioid agonist SNC80 in rhesus monkeys." Pharmacol Biochem Behav 85, 428-34 (2006).doi:10.1016/j.pbb.2006.09.012.

Jutkiewicz, E. M. et al., "The convulsive and electroencephalographic changes produced by nonpeptidic delta-opioid agonists in rats: comparison with pentylenetetrazol." J Pharmacol Exp Ther 317, 1337-48 (2006).doi:10.1124/jpet.105.095810.

Bausch, S. B. et al., "The delta opioid receptor agonist, SNC80, has complex, dose-dependent effects on pilocarpine-induced seizures in Sprague-Dawley rats." Brain Res 1045, 38-44 (2005).doi:10.1016/j.brainres.2005.03.008.

Codd, E. E. et al., JNJ-20788560 [9-(8-azabicyclo[3.2.1]oct-3-ylidene)-9H-xanthene-3-carboxylic acid diethylamide], "a selective delta opioid receptor agonist, is a potent and efficacious antihyperalgesic agent that does not produce respiratory depression, pharmacologic tolerance, or physical dependence." J Pharmacol Exp Ther 329, 241-51 (2009).doi:10.1124/jpet.108.146969.

Kouchek, M. et al., "Effects of intrathecal SNC80, a delta receptor ligand, on nociceptive threshold and dorsal horn substance p release." J Pharmacol Exp Ther 347, 258-64 (2013).doi:10.1124/jpet.113.206573.

Wang, H. B. et al., "Distinct subcellular distribution of deltaopioid receptor fused with various tags in PC12 cells." Neurochem Res 33, 2028-34 (2008).doi:10.1007/s11064-008-9678-9.

Petaja-Repo, U. E. et al., "Distinct subcellular localization for constitutive and agonist-modulated palmitoylation of the human delta opioid receptor." J Biol Chem 281, 15780-9 (2006).doi:10.1074/jbc.M602267200.

Kim, K. A. et al., "Neurotrophin-regulated sorting of opioid receptors in the biosynthetic pathway of neurosecretory cells." J Neurosci 23, 2075-85—(2003).

Commons, K. G. et al., "Cellular and subcellular localization of delta opioid receptor immunoreactivity in the rat dentate gyrus." Brain Res 738, 181-95 (1996).

Stewart, P. E. et al. "Activation of spinal delta-1 or delta-2 opioid receptors reduces carrageenan-induced hyperalgesia in the rat." J Pharmacol Exp Ther 268, 701-8 (1994).

Cahill, C. M. et al., "Up-regulation and trafficking of delta opioid receptor in a model of chronic inflammation: implications for pain control." Pain 101, 199-208 (2003).

Fraser, G. L. et al., "Antihyperalgesic effects of delta opioid agonists in a rat model of chronic inflammation." Br J Pharmacol 129, 1668-72 (2000).doi:10.1038/sj.bjp.0703248.

Brainin-Mattos, J. et al., "Cancer-related bone pain is attenuated by a systemically available delta-opioid receptor agonist." Pain 122, 174-81 (2006).doi:10.1016/j.pain.2006.01.032.

Kabli, N. et al., "Anti-allodynic effects of peripheral delta opioid receptors in neuropathic pain." Pain 127, 84-93 (2007).doi:10.1016/j.pain.2006.08.003.

Bodnar, R. J., "Endogenous opiates and behavior: 2011." Peptides 38, 463-522 (2012).doi:10.1016/j.peptides.2012.09.027.

Dipilato, L. M. et al., "Fluorescent indicators of cAMP and Epac activation reveal differential dynamics of cAMP signaling within discrete subcellular compartments." Proc Natl Acad Sci U S A 101, 16513-8 (2004).doi:10.1073/pnas.0405973101.

Li, Y. et al., "Pretreatment with phosphatase and tensin homolog deleted on chromosome 10 (PTEN) inhibitor SF1670 augments the efficacy of granulocyte transfusion in a clinically relevant mouse model." Blood 117, 6702-13 (2011).doi:10.1182/blood-2010-09-309864.

Miesenbock, G. et al., "Visualizing secretion and synaptic transmission with pH-sensitive green fluorescent proteins." Nature 394, 192-5—(1998).

Szent-Gyorgyi, C., et al., "Fluorogen-activating single-chain antibodies for imaging cell surface proteins." Nat Biotechnol 26, 235-40 (2008).doi:10.1038/nbt1368.

Global Industry Analysts, Inc., Analysts, G. I. & Inc. Global Pain Management Market to Reach US$60 Billion by 2015, According to a New Report by Global Industry Analysts, Inc. PRWeb eBooks 1-3 (2011).

Zastrow, von, M., "A cell biologist's perspective on physiological adaptation to opiate drugs." Neuropharmacology 47, 286-292 (2004).

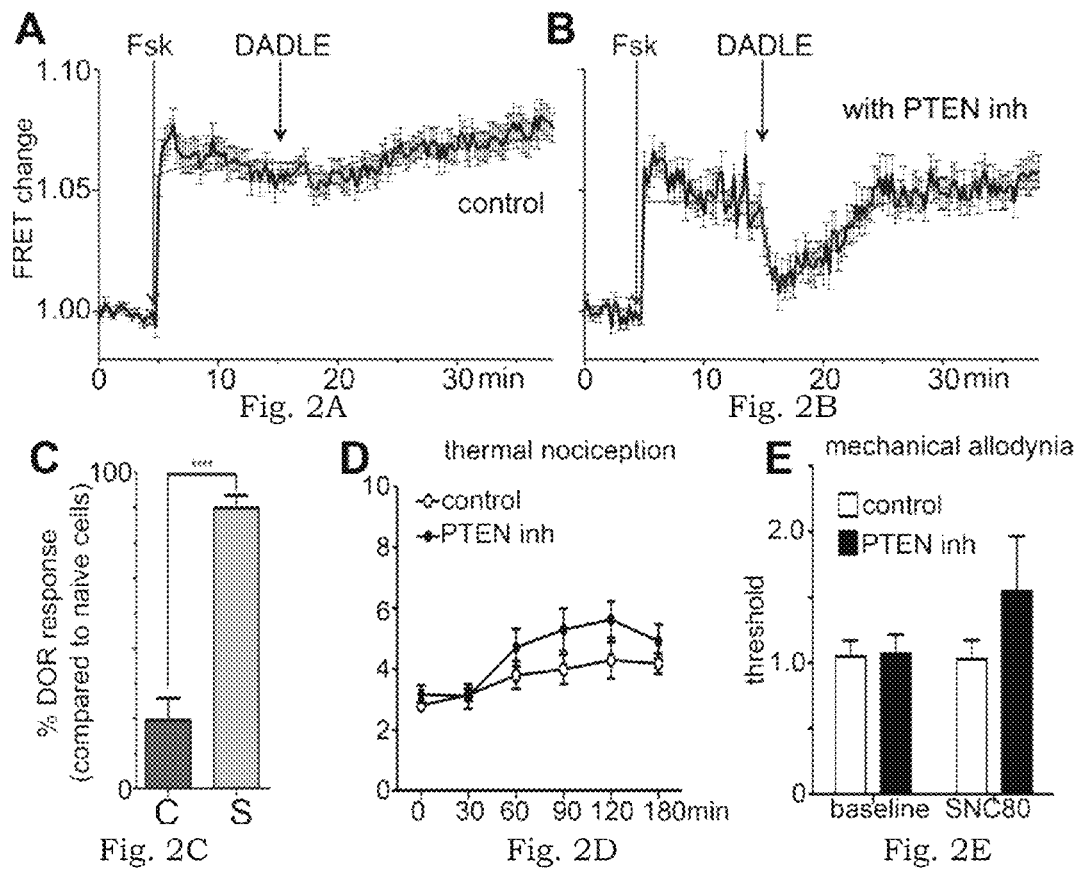
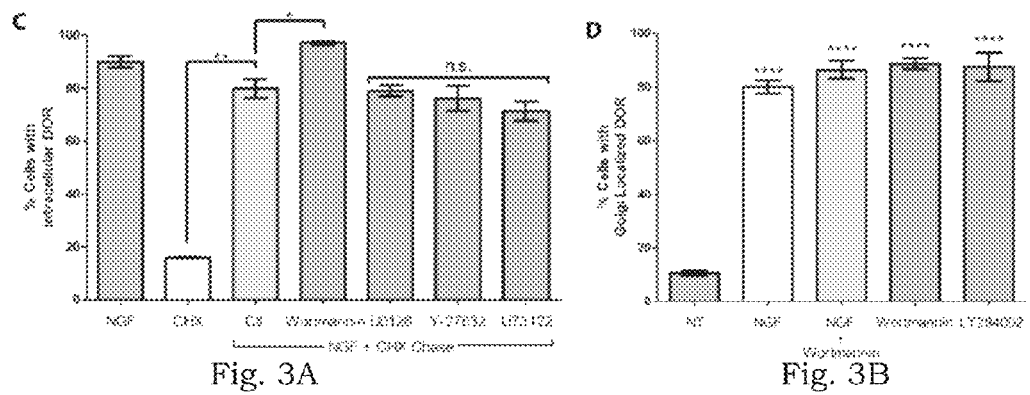

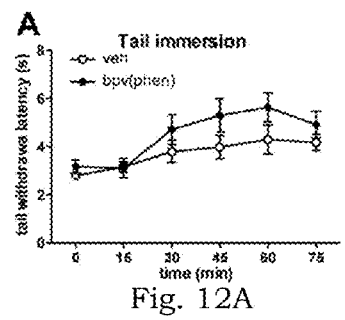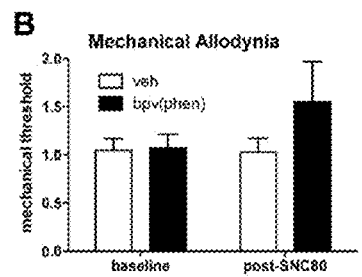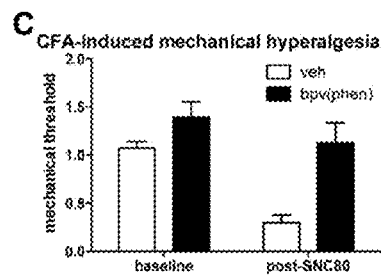
Fig. 12A    Fig. 12B    Fig. 12C
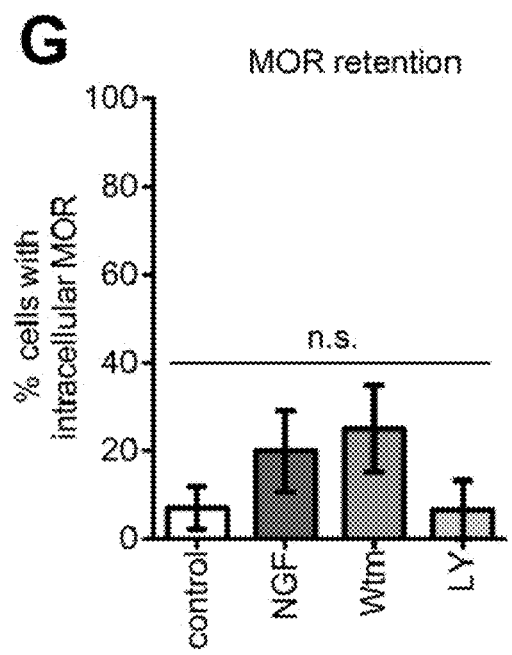
Fig. 13

METHOD TO INCREASE BIOAVAILABILITY OF THE DELTA-OPIOID RECEPTOR FOR MANAGEMENT OF PAIN AND NEUROPSYCHIATRIC DISORDERS

CROSS-REFERENCE TO RELATED APPLICATION

This application claims the benefit under 35 U.S.C. §119 of U.S. Provisional Application Ser. No. 61/999,021, filed Jul. 14, 2014, which is incorporated herein by reference.

FIELD OF THE INVENTION

This invention relates generally to a method for increasing the bioavailability of the delta-Opioid Receptor (DOR) for management of pain and neuropsychiatric disorders. More specifically, the invention relates to a method for inducing the surface trafficking of DOR in neurons by identifying drug-targetable enzymes that contribute to DOR retention and reduced surface expression, and driving DOR to the surface of central and peripheral neurons, thereby allowing DOR agonists to be used at lower effective doses, including as peripheral or systemic analgesics without adverse effects.

BACKGROUND

Chronic pain is estimated to cost the U.S. economy approximately $635 billion per year, with over $300 billion of this being direct costs for medical care. This surpasses the total US expenditure for heart disease, cancer, and diabetes combined. Pain is the most prevalent symptom presented at hospitals, and over 1.5 billion people in the world, and 116 million people in the United States, suffer from chronic pain. All people are at risk of chronic pain, and patients suffering from chronic pain experience a significant reduction in their quality of life. Additionally, pain is comorbid with the diseases mentioned above and many others, such as gastrointestinal disease, arthritis, and neuropsychiatric disorders, complicating the management of these diseases.

Pain has been managed primarily by opioid drugs for over two centuries, but their use is highly limited by adverse effects. Morphine, isolated in 1806, is still the mainstay of our management of pain. Morphine activates the mu-opioid receptor (MOR) in the nervous system. Over the last hundred years, we have generated over a thousand different analogs that activate the same target receptor, which potentially can act as effective analgesics for acute pain relief. In practice, however, the use of these drugs has been highly complicated by the rapid development of adverse effects. These include symptoms such as nausea, constipation, and dizziness, as well as the serious side effect of the development of addiction to opioid drugs. Patients develop tolerance (i.e., they need higher and higher doses to get the same analgesic effect) and dependence (i.e., they get adverse "withdrawal" symptoms in the absence of drug) to these drugs. There is no real strategy to treat addiction, and it is a major socioeconomic problem in the world today.

Addiction to opioids is a highly prevalent and comorbid disease that adds an additional cost to pain management. An estimated 10-15 million people in the US are addicted to prescription opioids, causing an additional revenue loss of $193 billion per year, with about $11 billion in healthcare costs. This is a rising trend for the future, with 26% of adolescents in schools reporting the use of illicit drugs in 2013. Overall, 52 million (i.e., 1 in 6) adults in the US have used prescription opioids without pain symptoms or a prescription, and 1 in 15 of these is expected to try heroin in the next 10 years. Consistent with this trend, opioid overdose deaths have shown almost a 100% increase over the last 10 years, up to 16,000 in 2010. Currently, the only method of managing addiction is to maintain the patient on methadone, often considered a less harmful alternative. This is far from ideal, and is further complicated by lack of patient compliance and an increased risk of abuse and deaths from methadone in the recent years.

The analgesic and addictive effects of MOR activation have not been separated, despite many years of efforts following different hypotheses. Addiction arises from the fact that MOR also activates the reward pathway in the brain, causing dependence of the patient to opioids. Peripherally restricted opioids have been tried to counter this, but they are only partially effective, and also initiate severe adverse effects. A second aspect of addiction is tolerance, where increasing doses are required to generate the original efficacy. Development of dependence and tolerance severely limit the long-term use of opioids in chronic pain. Importantly, the thousands of opioid analogs that have been generated, as part of a decades-long drive to find a non-addictive analgesic, all share the same limitations. Therefore, the identification of an alternate target for managing pain will have an immediate and profound socioeconomic impact.

The delta-Opioid Receptor (DOR) has been long-considered a promising alternate target for pain relief. DOR agonists are relatively non-addictive, and have much fewer adverse effects, because they are thought to not activate the reward pathway. The exact contribution of DOR-expressing neurons towards different modalities of antinociception is still being explored, but it is clear that these neurons mediate at least the main modalities such as mechanical pain. At a molecular level, DOR acts through the same pathways as MOR, reducing cAMP (cyclic adenosine monophosphate) and inhibiting $Ca^{2+}$ channels, and opening $K^+$ channels, to hyperpolarize and inhibit neurons. Although DOR agonists have relatively similar efficacies as MOR agonists in isolated systems, administrations of either peripheral (e.g., DADLE, loperamide) or central (e.g., SNC-80) agonists have poor analgesic responses in vivo. Further, at high concentrations, centrally acting DOR agonists can minimally inhibit pain, but also induce adverse side effects like convulsions, though a few DOR agonists have recently been developed that do not show such unwanted side effects. But the lack of effectiveness in vivo remains the limiting factor in targeting DOR for pain management.

Additionally, DOR dysfunction might also play roles in depression and related neuropsychiatric disorders. But drugs targeting this receptor have not been effective in vivo. There are four aspects to the current understanding of DOR:

1) Published data (since about the mid-2000's) indicate that most of the DOR in a neuron is kept in intracellular "storage" pools, and is not present on the surface. DOR is retained in intracellular locations in neurons in the periaqueductal gray and the dorsal horn of the spinal cord, areas that are important for pain sensation, with limited expression on the surface. As DOR needs to be on the cell surface to bind drugs and activate surface-localized effectors (e.g., adenylate cyclase) and analgesic pathways, this lack of surface localization could be a major contributor to the low effectiveness of DOR agonists, preventing efficient analgesia in vivo.

2) DOR agonists that can cross the blood brain barrier cause adverse reactions like convulsions at doses that are effective as analgesics. DOR agonists that cannot cross the blood brain barrier (i.e., peripherally restricted agonists) have not been effective, but it is not clear whether this is due to low availability of DOR in peripheral neurons.

3) In conditions of chronic pain, there is an increase in total expression of DOR, which leads to a proportionally higher amount being available on the surface, and therefore a proportional increase in efficiency for DOR agonists. Consistent with this, there is a correlation in an increased DOR expression on the surface, induced by pathological conditions such as inflammation or substance abuse, to better analgesic/antinociceptive effects of DOR agonists. Typically, such scenarios (e.g. inflammation), are thought to "prime" neurons to DOR agonists by increasing total DOR expression, and, therefore, proportionally increasing the amount on the neuronal surface, allowing DOR agonists to reduce hyperalgesia and relieve allodynia. Even in these cases, the effect is still less than clinically useful efficiencies. However, this leads to the hypothesis that, if one can find strategies to force DOR delivery to the neuronal surface, it will be an efficient alternate target for managing pain.

Importantly, while these speak to the feasibility of increasing DOR on the surface to target pain, there has been no previous attempt to change the trafficking of DOR to increase the proportion of surface DOR under normal situations. This is largely because the mechanisms regulating DOR trafficking and surface delivery have been poorly understood.

In addition, it is known that physiological responses of cells to changes in the extracellular environment rely on the precise localization of transmembrane receptors. Due to the amount of energy required for synthesis and trafficking of new proteins from the endoplasmic reticulum to the surface, one might intuit that the cell would re-use these receptors multiple times. While many receptors are recycled and re-used, however, this is not always the case. Many receptors are delivered to the cell surface and activated just once, before being destroyed. Whether a receptor is "multi-use" or "single-use" is determined by specific protein sequences on the receptors that result from small genetic variations between otherwise similar proteins.

Relevant examples of proteins with similar function, but different trafficking characteristics are the mu- and delta-Opioid Receptors (MOR and DOR), each part of the $G_i$-coupled G Protein-Coupled Receptor (GPCRs) subtype. In each case, the activated Ga subunit decreases the activation of adenylyl cyclase and cyclic-AMP production inhibiting signaling pathways within the cell. Additionally, activation of the opioid receptors inhibits calcium channel influx and promotes potassium channel efflux resulting in neuronal hyperpolarization that inhibits action potential initiation.

Opioid receptors are typically activated in our nervous system by endogenous endorphin or enkephalin agonists or by an exogenous opioid. While both opioid receptors can mediate pain inhibition, the mu-Opioid Receptor (MOR) has been more commonly targeted for drug development, and MOR agonists have been far more effective. Upon activation by an exogenous opiate agonist, MOR signaling is activated, and receptors are removed from the cell surface via endocytosis and transferred to intracellular endosomes. This leads to the loss of sensitivity of neurons to MOR agonists, because the surface receptor number is reduced. From the endosome, however, MOR is recycled to the cell surface for another round of agonist binding and signaling. Therefore, this recycling is key for recovery of the sensitivity of neurons to signaling by drugs that target MOR. In contrast, DOR's trafficking differs from MOR's trafficing in that after activation and endocytosis into the early endosome, it is excluded from recycling and instead is targeted to the lysosome where it is degraded. Therefore, DOR is a prototypical "single-use" receptor. Importantly, in order to obtain more DOR on the cell surface, newly synthesized receptors must be synthesized, trafficked through the biosynthetic pathway, and delivered to the cell surface.

Because the biosynthetic pathway regulates the sensitivity of neurons to DOR, unlike MOR, the delivery of the DOR from intracellular stores, as mentioned above, is critical. This difference in trafficking between DOR and MOR might be clinically relevant in chronic pain therapy, because the increased MOR desensitization and tolerance seen with habitual opiate administration is associated with changes in MOR endocytic trafficking and recycling. Thus, due to DOR's single-use characteristics, targeting of DOR might, among other treatments, provide a method to circumvent the potential addictive tendencies of opiates arising from MOR desensitization. The critical limitation is that the bioavailability of DOR on the surface of neurons, where they can be activated by drugs, is limiting, because DOR is stored in intracellular pools in neurons. Therefore, a method whereby the retained pool of intracellular DOR can be released and transported to the cell surface is desirable.

As such, a need exists to increase the bioavailability of DOR, and, in particular, to inducing the surface trafficking of DOR in neurons. The present invention addresses this need by (1) identifying drug-targetable enzymes that contribute to DOR retention and reduced surface expression, and (2) identifying a method to drive DOR to the surface of neurons. As a result, DOR agonists can be used at lower effective doses as peripheral or systemic analgesics. The DOR is also made more readily available for treatment of other disorders as well.

BRIEF SUMMARY OF THE INVENTION

The present invention increases the bioavailability of the delta-Opioid Receptor (DOR) by relieving DOR retention and inducing surface trafficking of DOR. The present invention also leverages the antinociceptive potential of DOR agonists to be analgesics without the adverse consequences normally associated with chronic treatment by MOR agonists.

The present invention identifies the signaling mechanism regulating intracellular DOR retention. By reversing the mechanism required for DOR retention, the present invention increases the surface trafficking of DOR, facilitating its activation by exogenous ligands. More specifically, the present invention has verified that, in one embodiment, phosphatase and tensin homolog (PTEN), a phosphatase that acts opposite PI3K, is a valid target for countering the PI3K inhibition and DOR retention seen in neurons. While DOR's dynamic trafficking characteristics have been reported previously, no prior research identifies PTEN, PI3K, or phospholipids as targets for regulating DOR translocation, and the present invention newly discloses that inhibiting PTEN or activating PI3K can directly stimulate DOR cell surface expression.

As such, one embodiment of the present invention is a method of stimulating delivery of DOR to the cell membrane or neural surface. By way of example, the present invention provides a method of inducing surface trafficking of DOR by interfering with the nerve growth factor (NGF) stimulated DOR retention using PI3K activators such as $740Y^{PDGFR}$. $740Y^{PDGFR}$ is a p85 regulatory subunit cell permeable activating peptide and, as demonstrated by the present invention, effectively prevents NGF-induced intracellular DOR retention.

Another embodiment of the invention is a validation protocol for a method of increasing the analgesic effectiveness of DOR agonists, as well as other neurological treatments, via stimulated delivery of DOR to the cell membrane or neural surface. In one exemplary embodiment, the present invention validates that a DOR agonist provides a significant analgesic effect above the baseline when applied with PTEN inhibitor. This method and pathway of treatment may also be used for other neurological disorders, as well as for drug screening and development.

Yet another embodiment of the present invention is a method to screen a library of compounds to affect movement of DOR to the cell membrane or neural surface. More specifically, the present invention discloses a cell-based assay system to detect surface delivery of DOR in combination with a fluorescence imaging system, including spinning disk confocal imaging or total internal reflection fluorescence imaging, for live cells. Similarly, the present invention provides method for semiautomatic screening of new DOR agonists using publicly available molecular libraries and the described assay system, which can be extended to flow cytometry or other systems measuring surface DOR levels.

BRIEF DESCRIPTION OF THE DRAWINGS

Embodiments of the present invention will now be described, by way of example only, with reference to the accompanying drawings for the purpose of illustrating the embodiments, and not for purposes of limiting the invention, wherein:

FIG. 2A through FIG. 2E are a series of graphs showing data from an experiment involving stimulated DOR delivery.

FIG. 3A and FIG. 3B are a pair of graphs, the graph on the left showing that, following pretreatment with NGF for 1 hour followed by CHX for 1 hour, an increase is observed for the percentage of cells with intracellular DOR; the graph on the right shows that, based on image analysis and quantification, the percentage of cells with Golgi localized DOR increases upon inhibition of PI3K similar to NGF (n>100 cells each; mean±SEM; ****$P<0.0001$).

FIG. 12A through FIG. 12C show PTEN inhibition improves efficacy of SNC80 in mice.

FIG. 13 is a graph depicting MOR retention.

DETAILED DESCRIPTION OF THE INVENTION

Figure 1:
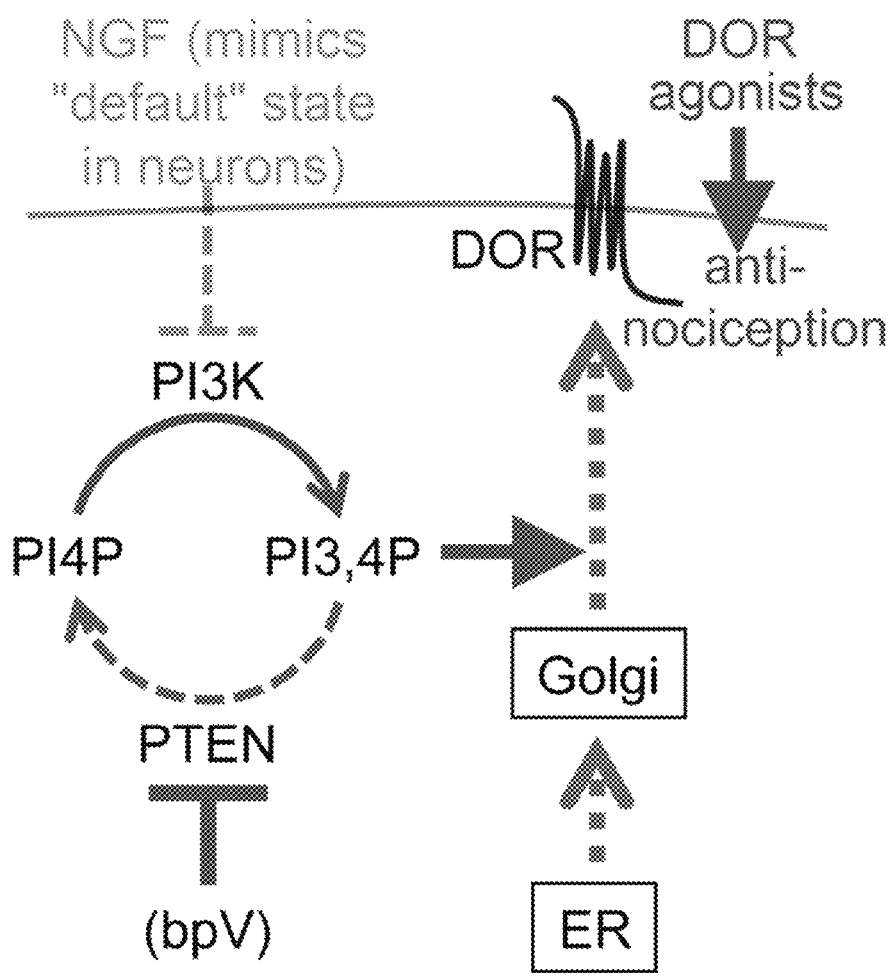
FIG. 1 presents a molecular model for restricted localization of DOR.

As shown in FIG. 1, the present invention identifies a targetable signaling axis that can be used to reprogram the surface expression of DOR, and provides a method for stimulating surface delivery of DOR in order to improve DOR signaling and antinociceptive effects. The present invention extends this principle to screen for translatable drugs that improve the efficacy of DOR analgesics to be used as convergent formulations for management of chronic pain.

Referring again to FIG. 1, a model for how phosphoinositide conversion at the Golgi regulates the availability of surface DOR is shown.

In particular, by reversing the mechanism required for DOR retention, the present invention increases the surface trafficking of DOR, facilitating its activation by exogenous ligands. For example, in one embodiment, the present invention uses phospholipids as valid targets for stimulating the surface delivery of DOR by removing the intracellular retention seen in neurons. By way of example, the present invention provides a method to activate the phospholipid kinase PI3K, which adds a phosphate group to the phospholipid PI(4)P and converts it to PI(3,4)P2, to induce surface trafficking of DOR, using 740YPDGFR, a PI3K activator. 740YPDGFR is a p85 regulatory subunit cell permeable peptide that activates PI3K, and, as demonstrated in this disclosure and the accompanying figures, effectively prevents DOR retention and increases surface DOR trafficking. Another example is the inhibition of PTEN, a phosphatase that counters the activity of PI3K by removing the phosphate group from phospholipids including PI(3,4)P2, as a method to directly stimulate DOR cell surface delivery and increase DOR bioavailability. While DOR's dynamic traffic character in response to agonists has been reported previously, no prior research identifies PTEN, PI3K, or phospholipids as specific targets for regulating DOR translocation.

In addition, the method is specific for DOR, as none of these methods increase the percentage of cells showing intracellular retention of MOR, as shown in FIG. 13. FIG. 13 shows the quantitation of the percentage of cells showing MOR retention (N>50 cells each; mean±SEM; no significant difference).

The method of the present invention can be demonstrated using an experimentally tractable system to model the retention, reprogramming, and surface delivery of DOR, using the PC12 rat neuroendocrine cell line. PC12 cells undergo neuronal specific signaling and differentiation in response to NGF. Using the method of the present invention, it has been confirmed an acute reprogramming of DOR trafficking occurs in PC12 cells in response to NGF, and identifies PI(3,4)P as an initial target for reprogramming DOR delivery in both PC12 cells and in neurons.

More specifically, the method uses PTEN inhibitors as a mechanism of increased efficiency of DOR agonists in signaling in cells and in nociception in animals. DOR is a Gi-coupled receptor that inhibits cAMP, and cAMP levels in cells can be measured as a direct indicator of DOR signaling. A FRET-based biosensor for measuring cAMP was optimized for real-time spatially resolved readout of cAMP signaling in PC12 cells. As shown in FIG. 2, PTEN inhibitors significantly increased DOR trafficking and inhibition of forskolin-induced increase in cAMP.

The first three graphs in FIG. 2 show the function response of DOR on the surface. An EPAC FRET sensor was used with live cell imaging under physiologic conditions of 37° C. The modulation of the cAMP activity was determined by performing a ratiometric analysis of an the donor fluorophore (Cyan Fluorescent Protein) image divided by the FRET image yielding a blue color for low cAMP and red for high cAMP. DOR was concomitantly visualized by fluorescent tagging. Addition of PTEN inhibitor significantly increased the capacity of neuralized cells to inhibit cAMP. The two images on the bottom-right of FIG. 2 show data in an experiment in which mechanical allodynia and tail withdrawal latency was performed in male C57BL6J mice 9-10 weeks old to determine the effects of the DOR agonist SNC-80 in the presence or absence of PTEN inhibition. PTEN inhibition alone did not induce an analgesic response. Following a 2 hour pretreatment with bpV(phen) (10 mg/kg), mechanical allodynia (Left) and tail withdrawal latency (Right) increased compared to vehicle control treated mice. All mice received SNC-80 (10 mg/kg IP). Additionally, pretreatment of mice with the PTEN inhibitor bpv(Phen) increased the antinociceptive effect of the DOR agonist SNC-80. Together, these methods can be used for stimulated DOR delivery as a convergent strategy for improving the efficacy of DOR agonists.

As detailed further below, PTEN inhibition increases the biopotency of DOR agonists. Importantly, this is the first clear report of a DOR agonist providing an analgesic effect above the baseline, as opposed to countering hyperalgesia by bringing the response back to baseline.

The following non-limiting example is provided to show the manner in which the methods of the present invention have been validated. This example is not intended to limit, in any manner, the process steps of the methods of the present invention, including without limitation, as to the order or timing of steps or the type of PTEN inhibitor that can be used.

EXAMPLE

The method of the present invention were validated by utilizing an in vivo mouse model, primary cultured Trigeminal Ganglion Neurons, and a relevant model for intracellular DOR retention using the neuroendocrine PC12 cell line combined with treatment of Nerve Growth Factor (NGF). In PC12 cells expressing a FLAG-tagged DOR, DOR is retained in the trans-Golgi network in response to NGF, resembling the phenotype observed in nociceptive neurons. To determine the mechanism regulating NGF-induced DOR retention, pharmacologic inhibition of known NGF-TrkA signaling molecules and quantification of the DOR localization via fixed cell immunofluorescence were employed. Activation of PI3-Kinase or inhibition of PTEN in primary Trigeminal Ganglion neurons released the effect of NGF. Further, inhibition of PI3K was required for the NGF induced retention of DOR, and was sufficient to induce its intracellular retention in the absence of NGF. Together, the results show that PI3K inhibition is required and sufficient for NGF-induced DOR retention, and implicates the regulation of a select phosphoinositide pool by the PI3K/PTEN activity balance. Additionally, the data demonstrates that in combination with PTEN inhibition, there is an increase in functional DORs on the cell surface that can now be utilized as a non-traditional target for pain therapy.

Example Results

1. DOR is INTERNALLY Localized in Primary Trigeminal Ganglion Neurons.

For a cell surface receptor to bind an endogenous or exogenous agonist, a fundamental prerequisite is their cell surface localization. Often, one can even predict the potential magnitude of an agonist response by determining the surface availability of the receptor. For many GPCRs, including the mu-Opioid Receptor, default receptor trafficking results predominately in cell surface localization. The delta-Opioid Receptor is unique, in neuronal cells it undergoes regulated biosynthetic trafficking during its transit from the Golgi apparatus to the plasma membrane. Following new receptor translation and exit from the endoplasmic reticulum, where DOR is made in cells, DOR is retained and localized within the trans-Golgi network. It remains held in this location until a signal for release can allow for bulk surface trafficking of the retained pool of receptors. The exact retention and release mechanism is unknown; however, addition of Nerve Growth Factor or NGF to the neuroendocrine PC12 cells can initiate internal retention of DOR, and bulk depolarization KCl can induce DOR surface trafficking.

In previous studies, overexpression with a Signal Sequence Flag-tag (SSF) DOR in hippocampal neurons exhibited an intracellular localization phenotype for DOR. To begin the example, confirmation that SSF-DOR was internally retained and localized with the Golgi complex in primary Trigeminal Ganglion (TG) sensory neurons was desired. First, primary TGs from adult mice were isolated and cultured. The SSF-DOR DNA construct was then transiently transfected into cultured TGs for subsequent localization analysis. Using a fixed-cell immunofluorescence assay, the location of SSF-DOR with an Alexa-488 conjugated anti-Flag M1 antibody was visualized, and the receptor signal was compared to an antibody against the Golgi marker GPP130. The majority of the DOR signal was internally localized in primary TG neurons and had a high degree of colocalization with the GPP130 Golgi marker. More specifically, the PC12 cell line can be used to study and more easily manipulate the process of intracellular DOR retention observed in neurons via initiating internal retention of DOR upon NGF addition. PC12 cells expressing SSF-DOR have a membrane localized expression pattern with little to no Golgi colocalization when analyzed via fixed cell fluorescence confocal microscopy. Upon treatment of these cells with Nerve growth Factor (100 ng/µL NGF) for 60 min, DOR accumulates internally and can be observed to colocalize with the Golgi marker.

2. NGF Treatment Recapitulates Neuronal Localization of DOR in PC12 Cells.

Due to this inherent internal localization in the neuronal system and the increased difficulty of culturing primary neurons, the neuronal model was not ideal model for dissecting the molecular mechanism underlying internal retention of DOR. Alternatively, it was chosen to use the neuroendocrine PC12 cell line as the model system. In native PC12 cells, upon expression of SSF-DOR, the DOR primarily localizes to the plasma membrane. For example, following addition of NGF (100 ng/mL) for 1 hour, an internal accumulation colocalizing with the Golgi complex can be detected, resembling the phenotype observed in the primary TG neurons. In the presence of cycloheximide DOR is primarily localized to the cell surface with minimal cells having intracellular DOR.

Due to the fact that the TrkA receptor, NGF's primary target in PC12 cells, is required for the internal retention of DOR in PC12 cells, it was chosen to begin the mechanistic evaluation into the retention with known TrkA downstream signaling targets using the fixed cell immunofluorescence assay. As shown in FIG. 3, following 1 hour of NGF (100 ng/mL) in PC12 cells expressing SSF-DOR, 90% of transfected cells had internal localization of DOR. In addition, FIG. 3 shows that this effect can be increased further via inhibition of PI3K with Wortmannin (10 µM) (n>100 cells each; mean±SEM; *P<0.05, **P<0.01). To confirm that the NGF-induced internal localization is retention and not only due to increased protein production in response to NGF, the mechanistic evaluation was continued in the presence of Cycloheximide (CHX, 3 µg/mL) to inhibit new protein synthesis. After 1 hour of CHX treatment alone, 16% of SSF-DOR expressing PC12 cells demonstrated internal localization, with most cells having predominant membrane localization. When NGF was added 1 hour before CHX addition and chased for 1 hour, 80% of cells imaged had internal localization of DOR. Again referring to FIG. 3, for the evaluation of required downstream signaling targets, pharmacologic inhibition of TrkA effectors was performed to determine the pathway required for NGF-induced retention of DOR. Inhibition of common NGF-modulated TrkA targets ROCK (Y-27632 5 µM), MEK (U0126 10 µM), Akt (Akt1/2 Kinase Inhibitor, 500 nM), PLC (U73122 10 µM), PKC (Chelerythrine 10 µM), and cSrc (PP2, 500 nM) had no statistical effect on increasing or decreasing the NGF-induced retention of DOR (see FIG. 3, some data not shown). Notably, inhibition of PI3K (Wortmannin 10 µM) in combination with NGF resulted in 97% of cells with intracellular retention of DOR. Thus, it can be hypothesized that inhibition of PI3K is sufficient for the NGF-induced intracellular retention of DOR.

3. PI3K Inhibition is Sufficient to Induce Intracellular DOR in the PC12 Cell Line.

As shown in FIG. 3, the data reveals that inhibiting PI3K with Wortmannin (10 µM) in combination with NGF administration and a subsequent 1-hour CHX chase significantly increased the percentage of cells exhibiting internal retention of DOR. It was therefore sought to determine if inhibition of PI3K via treatment with Wortmannin alone was sufficient to induce intracellular retention of DOR using a fixed cell immunofluorescence assay. FIG. 3 (right-side graph) shows that PC12 cells expressing SSF-DOR under normal treatment conditions (NT) exhibited predominate membrane localization of DOR, with little to no apparent colocalization with the Golgi marker GPP130. Following 1 hour of NGF (100 ng/mL) 80% of cells imaged had internal localization of DOR that colocalized with the Golgi. In cells treated with both NGF (100 ng/ml) and the PI3K inhibitor Wortmannin (10 µM), 87% of cells showed internal localization of DOR. Again referring to FIG. 3, for cells treated with Wortmannin (10 µM) alone or another PI3K inhibitor, such as LY294002 (10 µM), 88% of cells had significant internal localization of DOR within the Golgi region. Quantification of the percentage of cells exhibiting Golgi localized DOR reveals a significant increase in the amount of Golgi localized DOR during PI3K inhibition as shown in FIG. 3. These data strongly suggest that PI3K inhibition via Wortmannin or LY294002 treatment is sufficient to localize DOR within the Golgi.

4. Inhibition of PI3K is Required for Internal Localization of DOR, and Activation of PI3K Relieves the Intracellular Retention.

Figure 4:
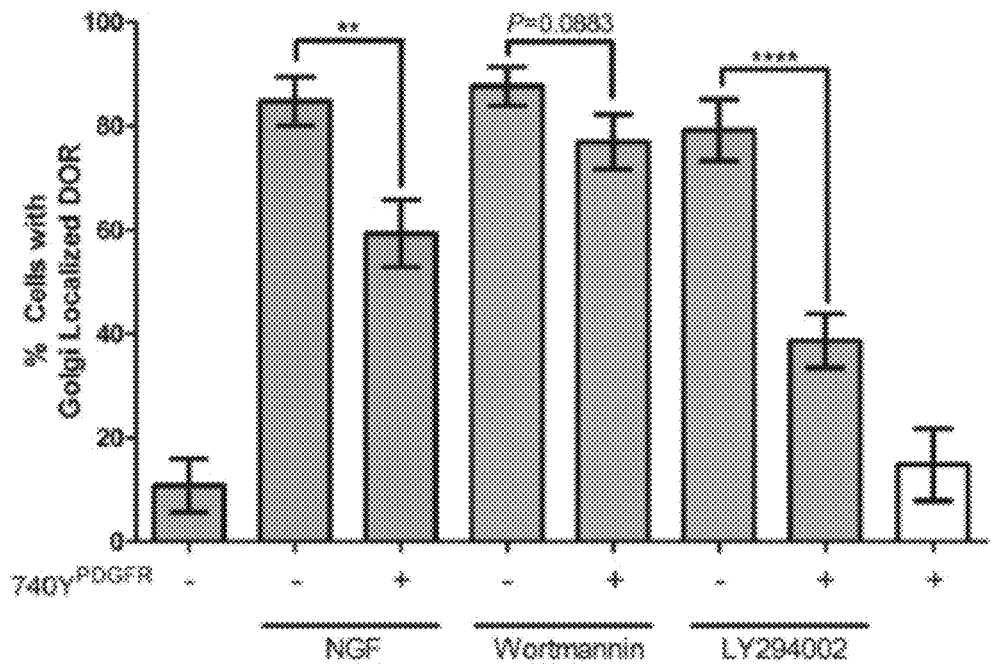
FIG. 4 is a graph showing that activation of PI3K by the p85 regulatory subunit cell permeable activating peptide 740Y$^{PDGFR}$ in combination with NGF prevents internal retention of DOR.
Figure 5:
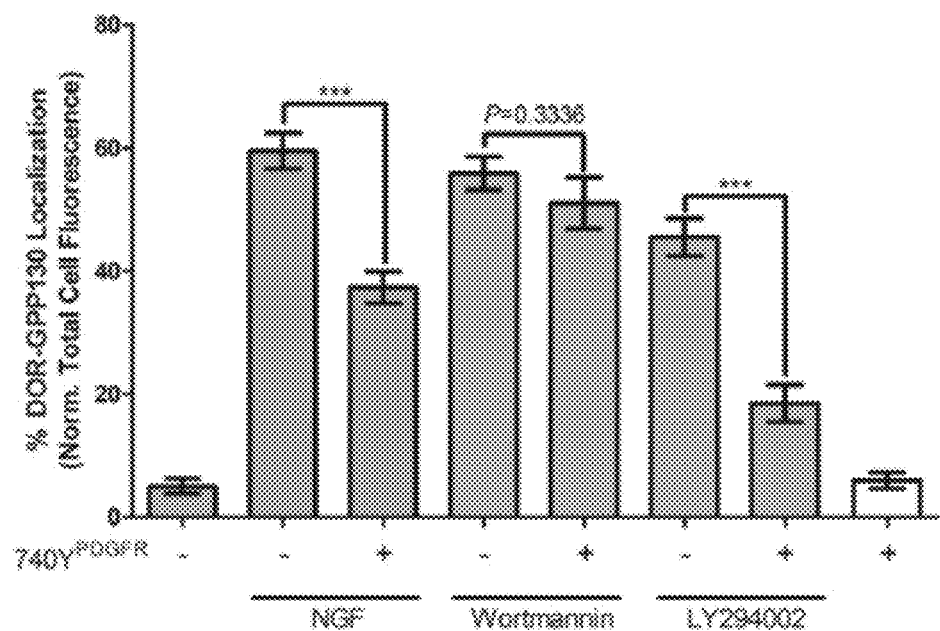
FIG. 5 is a graph showing that a significant decrease in the percentage of cells with GPP130 Golgi localized DOR after 740Y$^{PDGFR}$ addition occurred as compared to NGF and LY294002 treatment alone.

It has been determined that inhibition of PI3K is sufficient to induce intracellular retention DOR; however, it was not clear if PI3K inhibition was a requirement downstream of NGF-TrkA activation. To establish the requirement of PI3K inhibition for NGF induced retention of DOR, it was needed to directly activate PI3K in the presence of NGF. The PI3K activating peptide $740Y^{PDGFR}$ was utilized to elicit acute activation of the p85 regulatory subunit of PI3K. When combined with the irreversible PI3K inhibitor Wortmannin (10 µM), the $740Y^{PDGFR}$ (25 µg/mL) activating peptide does not abrogate the internal retention of DOR. However, when combined with the reversible PI3K inhibitor LY294002 (10 µM), the $740Y^{PDGFR}$ activating peptide significantly decreases the internal retention of DOR. As shown in FIG. 4 and FIG. 5, upon co-administration of NGF (100 ng/mL) and $740Y^{PDGFR}$ (25 µg/mL) in SSF-DOR expressing PC12 cells, there was a significant reduction of 38% in the percentage of cells with Golgi localized, as well as a reduction in the percentage DOR fluorescence localized to the Golgi compared to the total cell DOR fluorescence. By comparison, treatment with Wortmannin and 740Y$^{PDGFR}$ did not significantly decrease the percentage of Golgi localized DOR (n>100 cells each; mean±SEM; P<0.01, **P<0.0001). To determine the specificity of the reduction in DOR retention via 740Y$^{PDGFR}$ activating PI3K, the unique regulatory elements of PI3K and PI3K inhibitors were utilized.

PI3K is comprised of a p110 catalytic subunit and a p85 regulatory subunit. The 740Y$^{PDGFR}$ peptide binds to the p85 regulatory subunit and initiates kinase activity of the p110 catalytic subunit. Further, the PI3K inhibitor Wortmannin is an irreversible inhibitor of the p110 catalytic subunit and should not be influence by the 740Y$^{PDGFR}$ activating peptide; however, LY294002 is a reversible inhibitor of the p110 catalytic subunit and could be overcome by the 740Y$^{PDGFR}$ activating peptide. As shown in FIGS. 4-5, when PC12 cells were dually treated with Wortmannin (10 μM) and 740Y$^{PDGFR}$ (25 μg/mL) activating peptide there was a non-significant decrease in the internal retention of SSF-DOR compared to Wortmannin administration alone. FIGS. 4-5 further show that, when treated with LY294002 (10 μM) and 740Y$^{PDGFR}$ (25 μg/mL) activating peptide there was a 60% decrease in the internal retention of SSF-DOR compared to LY294002 administration alone. In addition, treatment of SFF-DOR expressing PC12 cells with the 740Y$^{PDGFR}$ (25 μg/mL) activating peptide alone has not effect on internal DOR retention compared to control treated cells. These results further support the conclusion that inhibition of PI3K by Wortmannin or LY294002 is sufficient to induce internal retention of DOR in PC12 cells, and demonstrate that PI3K inhibition is a required component downstream of NGF.

5. Inhibition of PI3K does not Affect Internalization of the Surface Pool of DOR.

Figure 6:
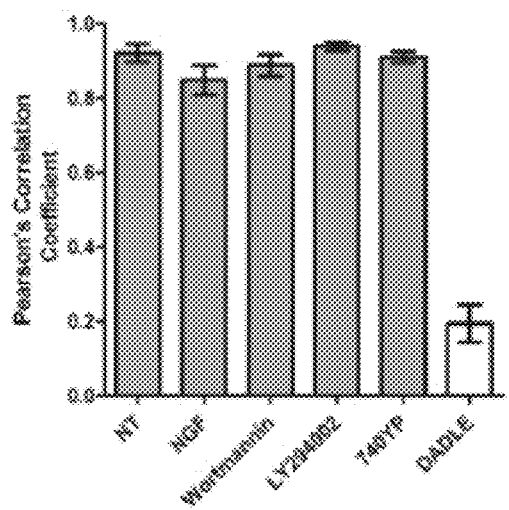
FIG. 6 is a graph showing that the colocalization of the primary and secondary antibody signal was determined using a Pearson's Correlation Coefficient, which demonstrated very significant colocalization for all of the pharmacologic treatments.

To eliminate the possibility that surface localized DOR was being actively internalized following PI3K inhibition, a fluorescence antibody internalization assay was performed in combination with pharmacologic inhibition of PI3K. SSF-DOR expressing PC12 cells were incubated with a cell-impermeable primary M1-Alexa 647 conjugated antibody to label the surface pool of receptors. The cells were treated with pharmacologic agents for 1 hour as in previous experiments, and receptor internalization was determined by adding a cell-impermeable secondary Alexa-488 conjugated antibody that recognizes the M1 primary antibody. The amount of internalization is quantified using a Pearson's Correlation Coefficient to determine the colocalization of the primary and secondary antibodies. If receptor internalization occurs, the primary antibody will not be accessible to the secondary antibody resulting in minimal antibody colocalization. Following 1-hour treatment with control (No Treatment), NGF (100 ng/mL), Wortmannin (10 μM), LY294002 (10 μM), or 740Y$^{PDGFR}$ (25 μg/mL) a very strong colocalization between the primary and secondary antibody was observed suggesting minimal internalization is occurring, as shown in FIG. 6. This was quantitated by calculating the Pearson's Correlation Coefficient revealed a very significant colocalization between the primary and secondary antibody localization for control, NGF, Wortmannin, LY294002, and 740Y$^{PDGFR}$ treated cells. As a positive control, the DOR agonist DADLE (10 μM) was added to induce activation and internalization of the receptor resulting in minimal antibody colocalization and a low Pearson's Correlation Coefficient, as shown in FIG. 6. This data demonstrate that pharmacologic activation or inhibition of PI3K within the timeframe of the assay does not induce the internalization of the surface pool of DOR. Further, it suggests that the internal accumulation of DOR upon inhibition of PI3K is due to retention at the TGN and not a result of internalized surface receptors.

6. PI3K Inhibition is Sufficient to Induce Retention of DOR, but not MOR.

Figure 7A:
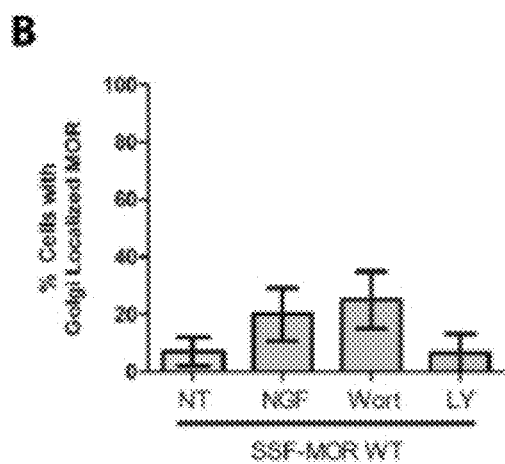
FIG. 7A through Fig. E are a series of graphs showing that, based on image analysis and quantification: (B) the addition of NGF or the PI3K inhibitors Wortmannin (10 μM) and LY294002 (10 μM) do not significantly increase the percentage of cells with Golgi localized MOR and do not increase the percentage of MOR localization within the Golgi marker GPP130 mask compared to the total cell fluorescence MOR fluorescence; (C) that inhibition of PI3K downstream targets do not result in a comparable increase in the percentage of cells with intracellular DOR; and (D) that inhibition of the 3' phosphoinositide phosphatase PTEN by SF1670 in combination with NGF treatment (100 ng/μL) can reduce the percentage of cells with Golgi localized DOR in a dose-dependent manner.
Figure 7C:
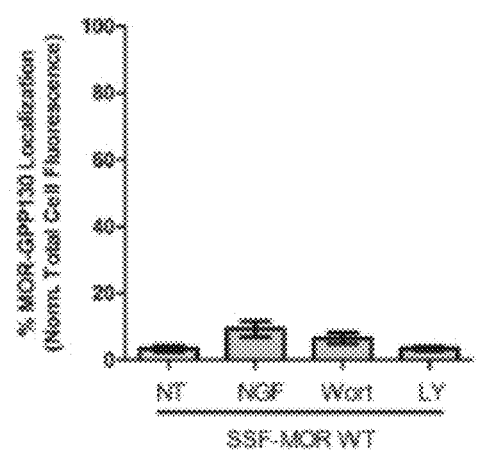
Figure 7D:
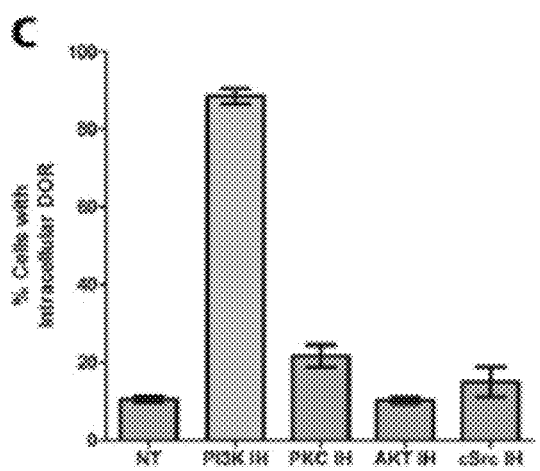
Figure 7E:
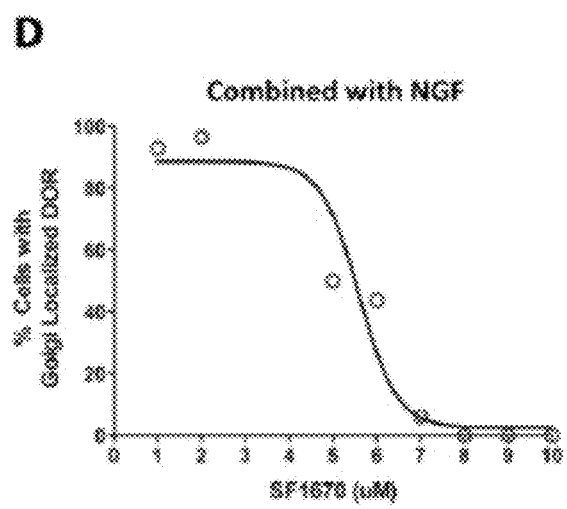

Previously, it was shown that the NGF-induced retention is specific to DOR and has minimal effect on MOR[37]. It was therefore asked if retention of DOR via PI3K inhibition was also specific to DOR. To determine this specificity, the sufficiency of NGF, and PI3K inhibition by Wortmannin or LY294002, to promote intracellular retention of SSF-MOR expressed in PC12 cells was evaluated using the fixed cell immunofluorescence assay. Under basal no treatment conditions, SSF-MOR was prominently localized to the cell surface. Upon NGF (100 ng/mL), Wortmannin (10 μM), or LY294002 (10 μM) treatment for 1-hour, the majority of the SSF-MOR signal was localization to the cell surface with minimal overlap within the Golgi region. FIG. 7A (top-left graph) demonstrates the analysis and quantification to determine the percentage of cells exhibiting Golgi localized MOR and the percentage of MOR fluorescence localization within the Golgi revealed a non-significant change in intracellular retention following treatment conditions.

7. Inhibition of PI3K Downstream Effectors is not Sufficient to Induce DOR Retention.

Together, the data indicate that PI3K inhibition is specific, required, and sufficient to induce intracellular retention of DOR; however, the mechanism by which PI3K induces this retention is not clear. PI3K, most well-known for its ability to phosphorylate the kinase Akt, can additionally regulate cellular processes by phosphorylating other kinases such as cSrc and PKC, and by promoting 3' phosphorylation of phosphoinositide species. It was hypothesized that if phosphorylation of downstream kinases within the PI3K pathway were required for intracellular regulation of DOR, pharmacological inhibition of these targets would be sufficient to induce DOR retention. As shown in FIG. 7A (top-right), using the fixed cell immunofluorescence assay in PC12 cells expressing SSF-DOR, a significant increase in the amount of cells exhibiting intracellular DOR following PI3K inhibition by Wortmannin (10 μM) was observed; however, treatment with the PKC inhibitor Chelerythrine (5 μM), cSrc inhibitor PP2 (10 μM), or Akt inhibitor Akt ½ kinase inhibitor (1 μM) did not significantly increase the intracellular retention of DOR. This suggests that induced-retention of DOR via inhibition of PI3K is not dependent upon the phosphorylation of common PI3K kinase signaling mediators Akt, PKC, and cSrc.

8. 3' Phosphorylation of Phosphoinositide is Required for Surface Delivery of DOR.

Figure 7B:
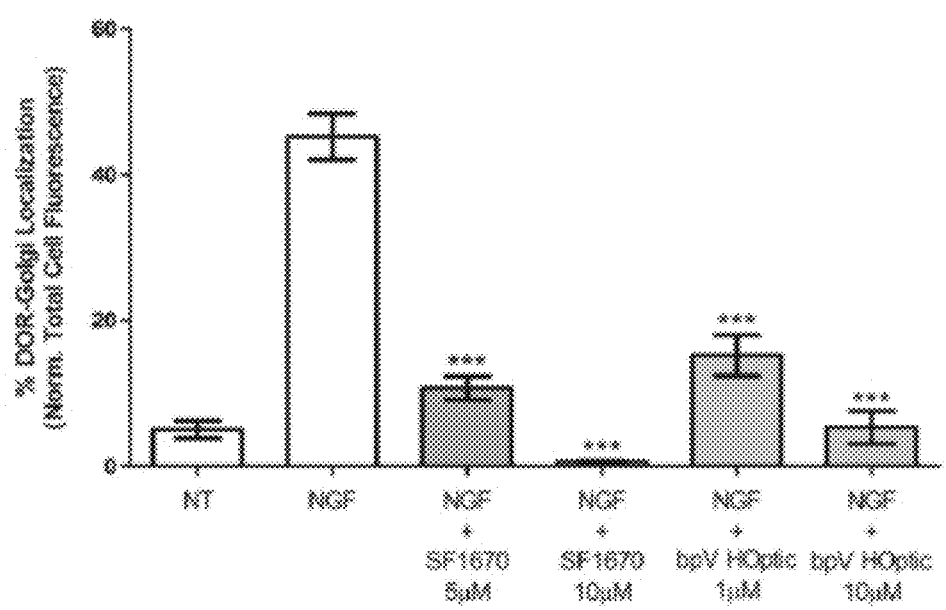

To determine the role of PI3K on DOR retention and surface delivery, the next focus was on evaluation the role of 3' phosphorylation of phosphoinositide species. The regulation of phosphorylation on phosphoinositide species within lipid membranes is a dynamic process involving both kinases and phosphatases. Specifically, for PI3K, the most notable opposing 3' phosphatase is the Phosphatase and Tension Homolog protein, PTEN. If 3' phosphorylation of phosphoinositide by PI3K is required for surface trafficking, it was hypothesized that inhibition of the phosphatase PTEN would promote surface delivery of DOR in the presence of NGF by decreasing the removal of 3' phosphorylation. FIG. 7A (bottom-right) graphically shows that, in PC12 cells expressing SSF-DOR and treated with NGF (100 ng/mL), the PTEN inhibitor SF1670 prevented NGF-induced retention of DOR in a dose dependent manner as assessed via fixed cell immunofluorescence. To further rule out nonspecificity due to off-target effects, another PTEN inhibitor, bpV(HOptic) (10 µM), was used and the previous experiments were repeated. The results obtained with both inhibitors reveal a striking inhibition of NGF-induced retention following PTEN inhibition. FIG. 7B shows that auantification of these data demonstrated dose-dependent inhibition of NGF-induced DOR retention as assessed by the percentage of cells exhibiting Golgi localized DOR and the percentage of DOR fluorescence localization within the Golgi normalized to the total cell DOR fluorescence. Taken together, these data suggest that 3' phosphorylation of a phosphoinositide species is required for NGF-induced DOR retention, and that inhibition of PTEN drives membrane localization of DOR.

8. The Balance Between PI(4)P and PI(3,4)P$_2$ Controls Retention and Surface Delivery of DOR.

Figure 8A:
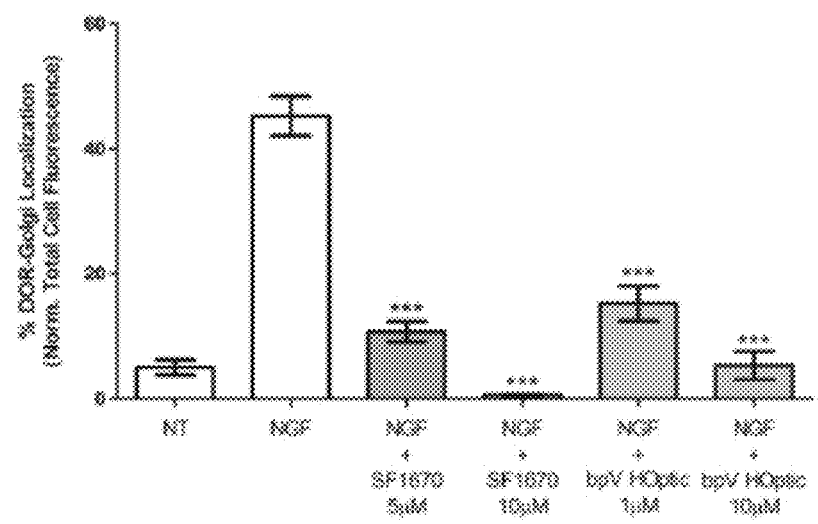
FIG. 8A through FIG. 8C are a series of graphs showing that, based on image analysis and quantification: significant reduction in the percentage of DOR fluorescence localized with the Golgi occurs as compared to the total DOR fluorescence in a dose-dependent manner (n>100 cells each; mean±SEM; *$P<0.001$); (H) that a significant increase in the percentage of cells with Golgi localized DOR as compared to the total DOR fluorescence (n>100 cells each; mean±SEM; *$P<0.001$); and (I) that a significant increase in the percentage of DOR fluorescence localized with the Golgi as compared to the total DOR fluorescence (n>100 cells each; mean±SEM; ***$P<0.001$).
Figure 8B:
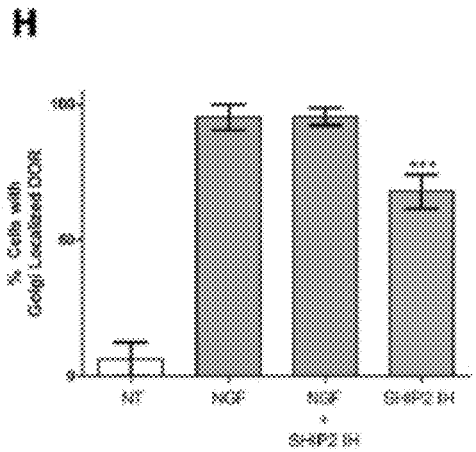
Figure 8C:
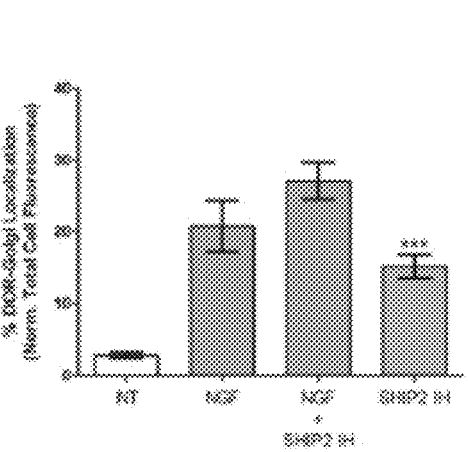

From the data, it can be concluded that the 3' phosphorylation of phosphoinositide is a required component for delivery of DOR to the cell surface. To determine compounds capable of phosphorylation, a reductionist approach was utilized comparing the results obtained during pharmacologic inhibition of phosphatases and kinases known to interact with 3' phosphorylation of phosphoinositides. Since PI3K inhibition was sufficient to induce retention of DOR, and PTEN inhibition was sufficient to prevent NGF-induced retention of DOR, the most likely phosphoinositides involved in retention were PI(4)P or PI(4,5)P$_2$, and the most likely phosphoinositides involved in surface delivery were PI(3,4)P$_2$ or PI(3,4,5)P$_3$. To differentiate between these possibilities the effects on DOR retention following SHIP2 inhibition, a 5' phosphatase, was evaluated. If SHIP2 inhibition promotes surface trafficking, PI(3,4,5)P$_3$ is the likely phosphoinositide required for surface delivery. If SHIP2 inhibition promotes DOR retention, PI(3,4)P$_2$ is the likely phosphoinositide required for surface delivery. PC12 cells expressing SSF-DOR were treated with NGF (100 ng/mL)+/−the SHIP2 inhibitor AS1938909 (10 µM). Referring to FIG. 8, in combination with NGF, SHIP2 inhibition was not significantly different than the DOR retention induced by NGF treatment alone. For cells treated only with the SHIP2 inhibitor, a significant increase in the percentage of cells exhibiting Golgi localized DOR, as graphically shown in FIG. 8 (lower-left), and, as shown in FIG. 8 (lower-right), the percentage of DOR fluorescence localization within the Golgi normalized to the total cell DOR fluorescence was observed. By using a reductionist approach, these data, in combination with the previous results, suggest that 3' phosphorylation of PI(4)P to PI(3,4)P2 is required for surface delivery of DOR.

9. Inhibition of PTEN Promotes Surface Expression of DOR in Neurons.

Figure 9A:
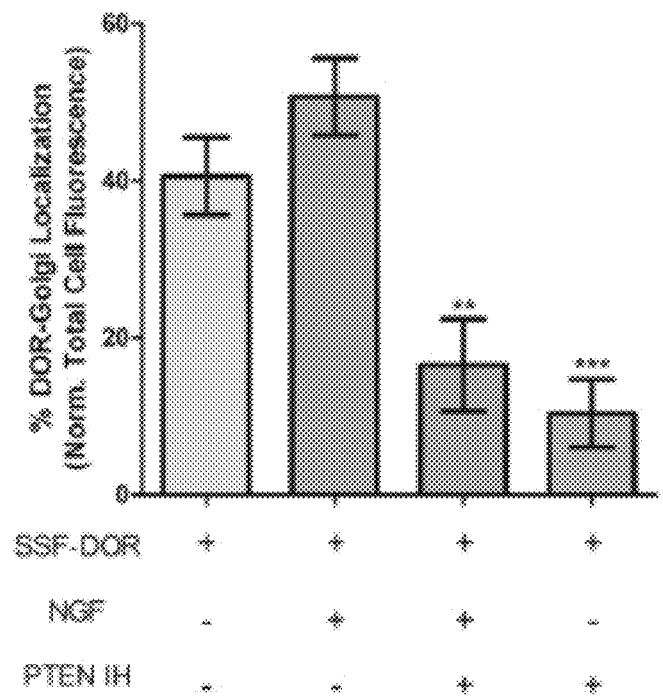
FIG. 9A and FIG. 9B are a pair of graphs showing that: the percentage of DOR fluorescence localized with the Golgi compared to the total DOR fluorescence decreased significantly upon treatment with SF1670 alone and in combination with NGF (n>10 neurons each; mean±SEM; $P<0.01$, *$P<0.001$); and that the colocalization between the DOR and GPP130 Golgi marker was determined using a Pearson's Correlation Coefficient, which demonstrated a significant increase in colocalization upon BGF treatment and a subsequent decrease in colocalization after PTEN inhibition (n>10 neurons each; mean±SEM; *$P<0.05$).
Figure 9B:
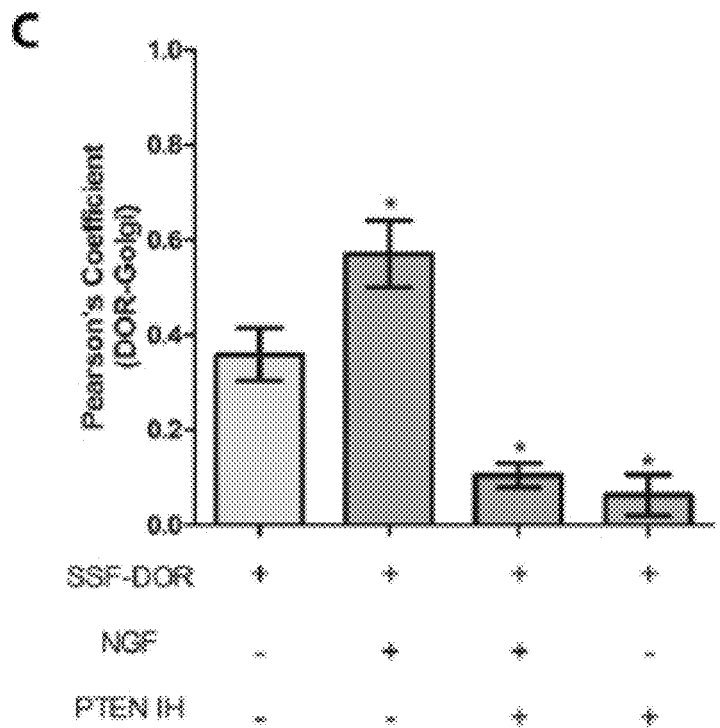

By using the neuroendocrine PC12 cell line as our model system, PTEN inhibition was identified as a tool to prevent the internal retention of DOR following NGF administration. This NGF-induced retention was assumed to recapitulate DOR's localization in nociceptive neurons; however, a direct evaluation of the effects following PTEN inhibition in primary neurons was required. For these experiments, nociceptive neurons from the Trigeminal Ganglion (TG) of adult mice were dissociated, cultured, and transfected with SSF-DOR. Fixed cell immunofluorescence experiments were performed to determine the localization of DOR with and without PTEN inhibition. An imaging analysis confirmed that in untreated control neurons, the majority of the DOR signal was co-localized within the Golgi compartment marker GPP130. NGF was added to the media to determine its effect on DOR localization in cultured TG neurons. Following NGF (100 ng/mL) treatment, as expected, DOR remained intracellularly localized. In both NGF and non-NGF treated neurons, PTEN inhibition resulted in a significant increase in the membrane localization of DOR, as showin in FIG. 9. Graphical quantification of the percentage of DOR localized within the Golgi compared to the total cell DOR fluorescence is shown in FIG. 9 (top), and the Pearson's Correlation Coefficient between the DOR fluorescence and the GPP130 Golgi fluorescence in FIG. 9 (bottom). PTEN inhibition resulted in an 85% decrease in the amount of DOR localized within the Golgi (see FIG. 9) and an almost complete elimination of the Pearson's correlation (see FIG. 9). These data support the results obtained using the PC12 cell line, and demonstrate that PTEN inhibition is sufficient to induce DOR surface expression in primary TG neurons.

10. Inhibition of PTEN Induces Surface Delivery of Functional DOR.

While PTEN inhibition visibly increases the cell surface localization of DOR, it was unclear whether the induced pool was actually a functional pool of receptors. To answer this question, the use of the cAMP biosensor, EPAC, was employed. DOR, a member of the G$_i$ G Protein-coupled family, functionally inhibits the production of cAMP following activation by its specific agonists. This effect on cAMP requires surface expression of functional receptors. Therefore, it was hypothesized that if PTEN inhibition was inducing the surface delivery of a functional pool of receptors, the cAMP inhibition following agonist addition will increase. The test began by testing the ability of the EPAC Förster Resonance Energy Transfer (FRET) sensor to detect the cAMP inhibition following activation of surface localized DOR in native PC12 cells. Relative quantification of the cAMP level was achieved by acquiring a confocal microscopy FRET image (405 nm excitation, 540 nm emission) and a GFP image (405 nm excitation, 470 nm emission). The ratio of the FRET image to the CFP image allows for the relative determination of the change in cAMP of time. Images were acquired in live cells at 37° C. to provide an appropriate physiological environment. Additionally, to visualize the surface pool of receptors and the point of activation via receptor internalization, the cells were pre-incubated with an Alexa-647 M1 antibody to recognize the surface SSF-DOR. In particular, imaging consisted of acquiring a FRET signal by excitation of 405 nm and emission of 535 nm, CFP signal by excitation of 405 nm and emission of 470 nm. The modulation of the cAMP activity was determined by performing a ratiometric analysis of the CFP image divided by the FRET image yielding a blue color for low cAMP and red for high cAMP. The surface SSF-DOR pool was visualized by labeling with an Alexa-647 conjugated primary antibody for the evaluation of endocytosis upon activation of the receptor to correlate with changes in cAMP activity.

Figure 10A:
FIG. 10A and FIG. 10B show a flow chart of the experimental procedure leading up to and during the cAMP imaging; and a graph showing that following Forskolin addition and cAMP increase, addition of DADLE results in activation of the new surface pool of DOR causing a significant inhibition of the Forskolin induced cAMP activity (n>20 cells each; mean±SEM; ****$P<0.0001$).
Figure 10B:
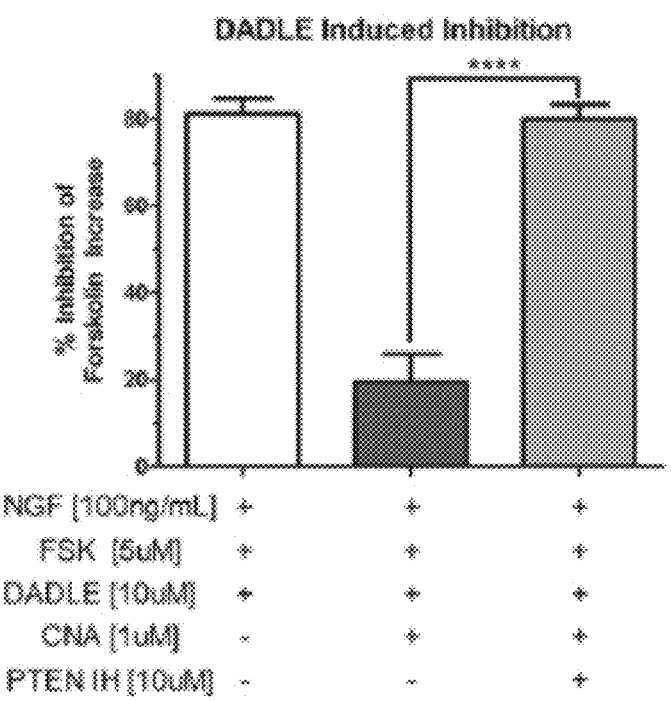
Figure 11A:
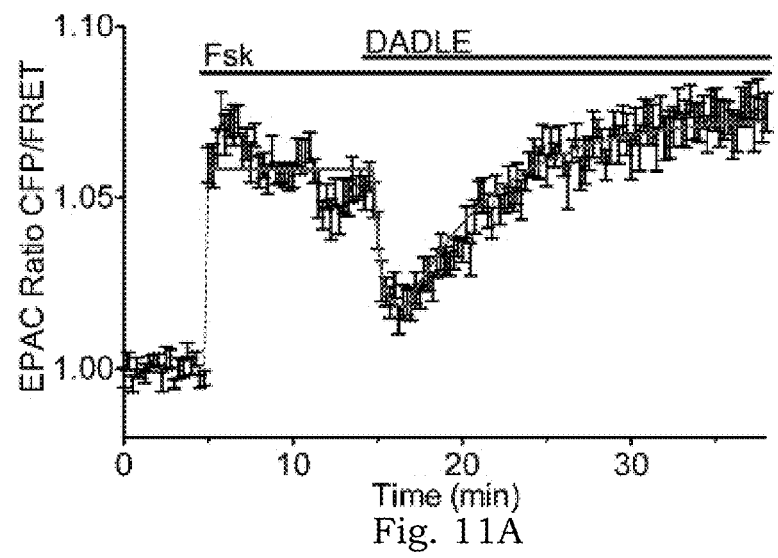
FIG. 11A through FIG. 11C are a series of graphs showing: (D) an average plot of the change in the cAMP level represented by the EPAC ratio from the CFP/FRET images normalized to the starting baseline, together with series of images for the DOR surface receptors and the EPAC ratio from example experiment; (E) the average plot of cAMP levels after blocking of the surface receptors with CNA demonstrates that there is little to no effect of adding DADLE once CNA has been added, together with a series of related images; and (F) following a washout of CAN and subsequent PTEN inhibition, addition of DADLE is now able to inhibit the increase in cAMP following Forskolin addition, together with a series of related images.
Figure 11B:
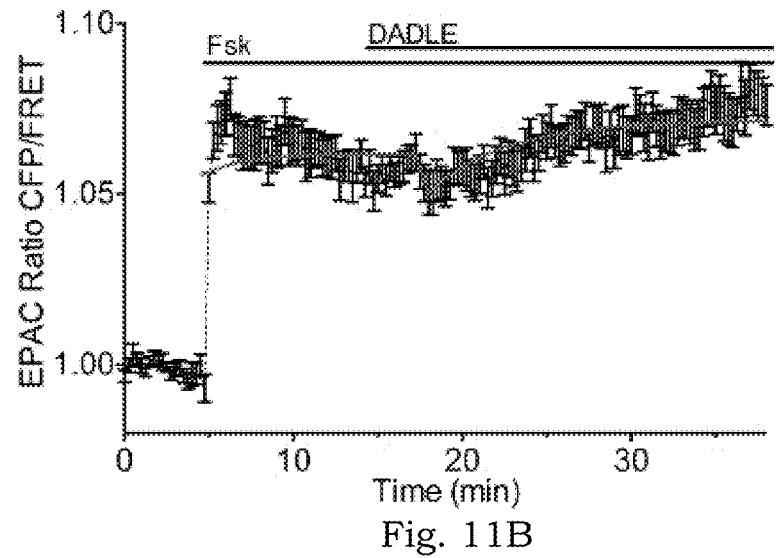
Figure 11C:
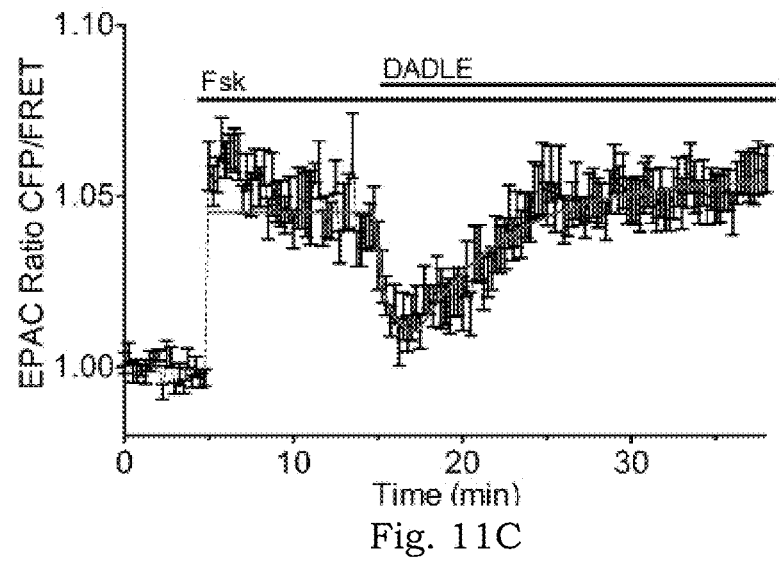

The experimental set-up for the cAMP evaluation is diagramed in FIG. 10 (left). In order to reproducibly quantify the decrease in cAMP following DOR agonist addition the baseline cAMP was increased through addition of a sub-maximal dosage of Forskolin (5 µM). Referring to FIG. 10 (right) and FIG. 11 (top), following NGF-pretreatment and increase in cAMP by Forskolin (5 µM), application of the DOR-specific agonist DADLE (10 µM) resulted in an 81% inhibition of cAMP. As part of this process, the Sub-maximal Forskolin (Fsk 5 µM) was used to stimulate cAMP levels above baseline. Following a 1 hour NGF (100 ng/µL) preincubation and Forskolin addition, activation of the surface pool of DOR with the agonist DADLE (10 µM)

resulted in a significant inhibition of the Forskolin induced cAMP activity. Upon inhibition of the surface pool of DOR with the irreversible antagonist chlornaltrexamine (CNA 1 μM) there was a minimal inhibition of the Forskolin induced cAMP activity upon DOR activation with the agonist DADLE. After the surface pool of DOR was inhibited with CNA and washed out, the PTEN inhibitor SF1670 (10 μM) was added to allow for trafficking of the retained pool of DOR. Next, FIG. 11 (middle) shows that quantification and analysis of the change in EPAC ratio following Forskolin and DADLE addition revealed a significant inhibition of cAMP after DADLE treatment and subsequent desensitization as the receptor underwent endocytosis. To next measure the reduction in cAMP following induced surface delivery of DOR, the signal produced by the receptors already present on the cell surface required removal. To effectively block functional signaling from the basal surface pool of receptors the irreversible antagonist chlornaltrexamine (CNA, 1 μM) was applied prior to performing the cAMP EPAC assay. Referring to FIG. 10, this cell impermeable compound is able to covalently bind to the surface receptor pool and significantly reduced inhibition of cAMP (19% inhibition) following DADLE addition. Quantification of the change in EPAC ratio following Forskolin and DADLE addition show minimal response after pretreatment with CNA, and reduced endocytosis of the receptor, as shown in FIG. 11 (middle). With the surface receptor pool functionally blocked, it was possible to measure the cAMP inhibition following induced surface delivery of DOR. After NGF pre-treatment and CNA blockade, the PTEN inhibitor SF1670 (10 μM) was added and the cAMP EPAC assay was performed. Referring again to FIG. 10, following the increase in cAMP induced by Forskolin addition, an 80% inhibition of cAMP upon DADLE treatment was now observed. This increased cAMP inhibition was 61% greater than the inhibition obtained after CNA alone. Referring to FIG. 11 (bottom), quantification of the change in EPAC ratio following Forskolin and DADLE addition shows a significant increase in the response after induced surface delivery via PTEN inhibition. By utilizing the EPAC FRET sensor in PC12 cells expressing SSF-DOR, we demonstrate that following NGF-induced internal retention, an increase in the functional inhibition of cAMP can be observed resulting from increased surface delivery of DOR.

11. Validation that Inhibition of PTEN Induces Surface Delivery of Functional DOR and Improves Analgesic Effects of DOR Agonists in Mouse Models of Pain.

Referring generally to FIG. 12, in vivo data show that PTEN inhibition improves efficacy of SNC80, a DOR agonist, in mice. In this experiment, thermal nociception was determined by using the warm water tail withdrawal assay, with a cut-off of 12 s at 52.5° C. water temperature. After 3 basal measurements, mice were injected with vehicle or bpv(phen)(10 mg/kg SC), and returned to their home cages. Four hours post-injection, tail immersion responses were determined and mice were injected with vehicle or SNC80 (10 mg/kg IP). They were subsequently tested every 15 minutes for 90 minutes. All animals were male C57bl6J mice of 9-10 weeks of age, n=8 per group. Mice without SNC80 did not show any significant deviation from the baseline. Mechanical allodynia was tested using standard protocols (such as the protocols disclosed by Pradhan et al., 2009, PMID: 1941254) on male C57bl6J mice 9-10 weeks old, n=8 per group. Mice were injected with vehicle or bpv(phen)(10 mg/kg), and tested four hours after for reduced allodynia in response to SNC-80. Mice treated with bpv (phen), but not control mice, showed a response. Mechanical hyperalgesia was tested in a CFA model for chronic pain. After baseline recordings, mice were injected with CFA (13 μl, intraplantar) and were tested 72 hours later. On the test day, mice received either bpv(phen)(10 mg/kg SC) or vehicle. Four hours later, mice were tested for response to a lower dose of SNC 80 (3 mg/kg IP). Mice treated with bpv(phen) showed a response to SNC80.

To determine the functional response of DOR on the surface on neurons in mice, the EPAC FRET sensor 45 was used with live cell imaging under physiologic conditions of 37° C. The modulation of the cAMP activity was determined by performing a ratiometric analysis of the CFP image divided by the FRET image yielding a blue color for low cAMP and red for high cAMP. DOR was concomitantly visualized by fluorescent tagging. Addition of PTEN inhibitor significantly increased the capacity of neuralized cells to inhibit cAMP. Mechanical allodynia and tail withdrawal latency was performed in male C57BL6J mice 9-10 weeks old to determine the effects of the DOR agonist SNC-80 in the presence or absence of PTEN inhibition. PTEN inhibition alone did not induce an analgesic response. Following a 2 hour pretreatment with bpV(phen) (10 mg/kg), mechanical allodynia and tail withdrawal latency increased compared to vehicle control treated mice. All mice received SNC-80 (10 mg/kg IP).

As shown next in FIG. 12 (left), thermal nociception was determined by using the warm water tail withdrawal assay, with a cut-off of 12 s at 52.5° C. water temperature. After 3 basal measurements, mice were injected with vehicle or bpv(phen)(10 mg/kg SC), and returned to their home cages. Four hours post-injection, tail immersion responses were determined and mice were injected with vehicle or SNC80 (10 mg/kg IP). They were subsequently tested every 15 minutes for 90 minutes. All animals were male C57bl6J mice of 9-10 weeks of age, n=8 per group. Mice without SNC80 did not show any significant deviation from the baseline. Next, referring to FIG. 12 (middle), mechanical allodynia was tested using standard protocols (for example, Pradhan et al., 2009, PMID: 1941254) on male C57bl6J mice 9-10 weeks old, n=8 per group. Mice were injected with vehicle or bpv(phen)(10 mg/kg), and tested four hours after for reduced allodynia in response to SNC-80. Mice treated with bpv(phen), but not control mice, showed a response. FIG. 10 (right) shows mechanical hyperalgesia in a CFA model for chronic pain. After baseline recordings, mice were injected with CFA (13 μl, intraplantar) and were tested 72 hours later. On the test day, mice received either bpv(phen)(10 mg/kg SC) or vehicle. Four hours later, mice were tested for response to a lower dose of SNC 80 (3 mg/kg IP). Mice treated with bpv(phen) showed a response to SNC80.

As such, the present invention provides a method of stimulating delivery of DOR to the cell membrane or neural surface. By way of example, the present invention provides a method of inducing surface trafficking of DOR by interfering the nerve growth factor (NGF) stimulated DOR up-regulation and cytoplasmic translocation with blockers for PI3K inhibitors such as $740Y^{PDGFR}$. $740Y^{PDGFR}$ is a p85 regulatory subunit cell permeable activating peptide and, as demonstrated by the present invention, effectively prevents NGF induced DOR internalization. The method of stimulating delivery of DOR to a cell membrane involves manipulation of phospholipids, by administration of a predetermined dosage of a PTEN inhibitor or PI3K activator. The PTEN inhibitor can be administered through known drug delivery systems, including oral administration, localized injection or intravenous administration. The predetermined dosage of the PTEN inhibitor can vary depending on the inhibitor used. Typically, stimulated delivery of DOR to the neural surface will start within 30 minutes of administration, with maximum effects observed between 3 and 6 hours after administration.

Another embodiment of the invention is a method of increasing the analgesic effectiveness of DOR agonists, as well as other neurological treatments, via stimulated delivery of DOR to the cell membrane or neural surface. In one exemplary embodiment, the present invention validates that a DOR agonist provides an analgesic effect above the baseline when applied with PTEN inhibitor. This method and pathway of treatment may also be used for other neurological disorders, as well as for drug screening and development. In use, this method involves application of a DOR agonist or other treatment, after delivery of DOR has been stimulated to the cell membrane of neural surface of a patient. The DOR agonist or other treatment is administered, by known drug delivery systems, after a predetermined period of time has passed after administration of the PTEN inhibitor. In a preferred embodiment, this period of time can range from 3 to 6 hours. This procedure can be repeated as needed. In particular, because DOR has a single release action, this procedure can be repeated to coincide to the time frame when the effects of the DOR agonist or other treatment begin to dissipate in a patient.

Yet another embodiment of the present invention is a method to screen a library of compounds to affect movement of DOR to the cell membrane or neural surface. More specifically, the present invention discloses a cell assay system to detect surface delivery of DOR in combination with a fluorescence imaging system, including spinning disk confocal imaging or total internal reflection fluorescence imaging, for live cells. Similarly, the present invention provides methods for semiautomatic screening of new agents that can drive DOR to the surface, and therefore increase the potency of DOR agonists, using publicly available molecular libraries and the described assay system, which can be extended to flow cytometry or other systems measuring surface DOR levels. One example method used in the embodiments described above is to directly visualize surface DOR levels using an antibody directed against the extracellular domain of the DOR. When applied to cells without permeabilizing (breaking apart) the cell using detergents, this will label only the DOR present on the cell surface. Additional antibody labeling with a different color after permeabilization will detect the intracellular pool of DOR, and a ratio of surface to internal pool will report the extent of surface expression of DOR. An additional example method for this assay is the development of a biosensor that determines the amount of delta opioid receptors on the cell surface, whereby a pH-sensitive green fluorescent protein (GFP) was attached to the extracellular domain of DOR. When expressed in cells, this fluorescent protein is quenched rapidly in the acidic environments of intracellular vesicles, causing only the surface DOR to be fluorescent. This was used as an assay to detect changes in surface DOR in living cells in the methods described. Because the assay relies on direct visualization of fluorescence without addition of dyes or other extra steps, this will be easily amenable to higher throughput screens.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A method of increasing bioavailability of delta-opioid receptors on a cell, comprising:
    regulating phosphorylation of a phospholipid in a cell by administering a drug affecting a phosphatase or a phospholipid to prevent intracellular retention of delta opioid receptors, wherein the drug is selected from the group consisting of bpV(phen), bpV(HOptic), and SF1670;
    thereby forcing delivery of the delta-opioid receptors to a surface of the cell.

2. The method of claim 1, wherein regulating phosphorylation of a phospholipid comprises:
    increasing a level of a 3' phosphorylated phospholipid.

3. The method of claim 2, wherein the 3' phosphorylated phospholipid is PI(3,4)P2.

4. The method of claim 2, wherein increasing the level of the 3' phosphorylated phospholipid comprises:
    activating PI3K.

5. The method of claim 1, wherein the the phosphatase is selected from the group consisting of:
    PI(4)P, PI(4)P regulators, PI(4)P effectors, PI(3,4)P2, PI(3,4)P2 regulators, PI(3,4)P2 effectors, PTEN, PTEN regulators, PTEN effectors, PI3K, PI3K regulators, and PI3K effectors.

6. The method of claim 1, wherein regulating phosphorylation of a phospholipid further comprises:
    converting PI(4)P to PI(3,4)P2 by 3' phosphorylation.

7. The method of claim 1, further comprising:
    administering a delta-opioid agonist, wherein the delta-opioid agonist targets the delta-opioid receptors forced to the surface of the cell.

8. A method of increasing bioavailability of delta-opioid receptors on a cell, comprising:
    regulating phosphorylation of a phospholipid in a cell by administering a drug affecting a PI3K to prevent intracellular retention of delta opioid receptors, wherein the drug is $740Y^{PDGFR}$;
    thereby forcing delivery of the delta-opioid receptors to a surface of the cell.

* * * * *